United States Patent [19]

Kolze

[11] Patent Number: 5,050,918

[45] Date of Patent: Sep. 24, 1991

[54] ACCESSORY FOR HOLDING A CONTACT LENS

[76] Inventor: Alicia A. Kolze, 10195 Sycamore St., Demotte, Ind. 47312

[21] Appl. No.: 518,190

[22] Filed: May 3, 1990

[51] Int. Cl.⁵ .............................................. A61F 9/00
[52] U.S. Cl. ..................................... 294/1.2; 294/64.1
[58] Field of Search ................. 294/1.2, 64.1; 206/5.1; 606/107; 433/31, 93; 132/301, 304, 316, 286

[56] References Cited

U.S. PATENT DOCUMENTS

| | | | |
|---|---|---|---|
| 2,823,455 | 2/1958 | Sprague | 433/93 |
| 2,861,342 | 11/1958 | Katz | 433/31 |
| 2,919,696 | 1/1960 | Rinaldy | 294/1.002 |
| 3,031,918 | 5/1962 | Moyers | 294/1.002 |
| 3,092,910 | 6/1963 | Warriner | 433/31 |
| 3,102,338 | 9/1963 | Warriner | 433/31 |
| 3,424,486 | 1/1969 | Corley | 294/1.002 |
| 3,897,968 | 8/1975 | Allen, Jr. | 294/1.002 |
| 3,934,914 | 1/1976 | Carruthers | 294/1.002 |
| 4,026,591 | 5/1977 | Cleaveland | 294/1.002 |
| 4,123,098 | 10/1978 | Shoup | 294/1.002 |
| 4,201,408 | 5/1980 | Tressel | 294/1.002 |
| 4,521,185 | 6/1985 | Cohen | 433/93 |

Primary Examiner—Johnny D. Cherry
Assistant Examiner—Cathleen G. Pringle
Attorney, Agent, or Firm—Terry M. Gernstein

[57] ABSTRACT

An accessory for holding a contact lens includes a concave element that is place adjacent to a user's cornea or adjacent to a contact lens on that user's cornea and a fluid circuit that connects an air passage in that concave element to the interior of a flexible hollow ball. Flexing the ball causes air to move out of the air passage to move a contact lens from the concave element onto a user's cornea, and release of a distorted ball sucks air into the air passage to move a contact lens off of a user's cornea onto the concave element. Guiding elements include mirrors and support arms.

1 Claim, 2 Drawing Sheets

ACCESSORY FOR HOLDING A CONTACT LENS

TECHNICAL FIELD OF THE INVENTION

The present invention relates to the general art of optometry, and to the paticular field of contact lenses.

BACKGROUND OF THE INVENTION

Contact lenses are being worn by more people, both young and old, today than ever before. Contact lenses vary from soft to hard, and can be extended wear or disposable, or something in between.

No matter what the type, all contact lenses have certain characteristics in common. For example, the lenses must be placed on the wearer's cornea for use and removed for storage, disposal or cleaning. This requires a user to touch the lens. It has been documented that, due to the warm and moist environment existing in the eye, the eye is a prime breeding ground for bacteria. Therefore, contact lens cleaning is essential to healthy eyes and comfort, and contact lenses should be cleaned well and often.

Most cleaning procedures require the wearer to handle the lens to remove it, to clean it and to re-insert it. Thus, the lenses must be touched while they are in the user's eye and when they are out of the user's eye.

While many contact lens wearers are quite adept at handling their lenses, some, especially the inexperienced contact lens wearer, are not. This makes the removal and insertion of contact lenses an onerous task for such people, and may inhibit proper care and wearing of such lenses.

Still further, even proficient contact lens wearers often do not clean their hands well enough prior to touching their lenses to ensure fully antiseptic conditions. Thus, the weak point in most contact lens cleaning procedures centers around the requirement that the wearer touch the lens with his or her hands some time during a cleaning or storing process.

Therefore, there is a need for an accessory for holding contact lenses which will facilitate insertion and removal of such lenses from a wearer's eye, even for inexperience or inept wearers, and which will permit cleaning of such lenses without requiring the user to touch the lenses with his or her hands.

OJBECTS OF THE INVENTION

It is a main object of the present invention is to provide an accessory for holding contact lenses which will facilitate insertion and removal of such lenses from a wearer's eye.

It is another object of the present invention to provide an accessory for holding contact lenses which will facilitate insertion and removal of such lenses from a wearer's eye even for inexperience or inept wearers.

It is another object of the present invention to provide an accessory for holding contact lenses which will facilitate insertion and removal of such lenses from a wearer's eye even for inexperience or inept wearers, and which will permit cleaning of such lenses without requiring the user to touch the lenses with his or her hands.

SUMMARY OF THE INVENTION

These, and other, objects are achieved by an accessory for holding contact lenses which permits a user to reliably hold contact lenses during insertion or removal of the lenses into or out of his eye, with requiring that user to touch the lenses with his or her hands.

The device includes a means for gently holding the lens during removal, insertion and cleaning as well as a means for guiding the lens into or out of the user's eye.

In this manner, the accessory facilitates insertion and/or removal of the lens, even for inept wearers, and permits the lens to be cleaned without requiring a user to touch the lens with his or her hands.

BRIEF DESCRIPTION OF THE DRAWING FIGURES

DETAILED DESCRIPTION OF THE PREFERRED EMBODIMENT OF THE INVENTION

Figure 1:
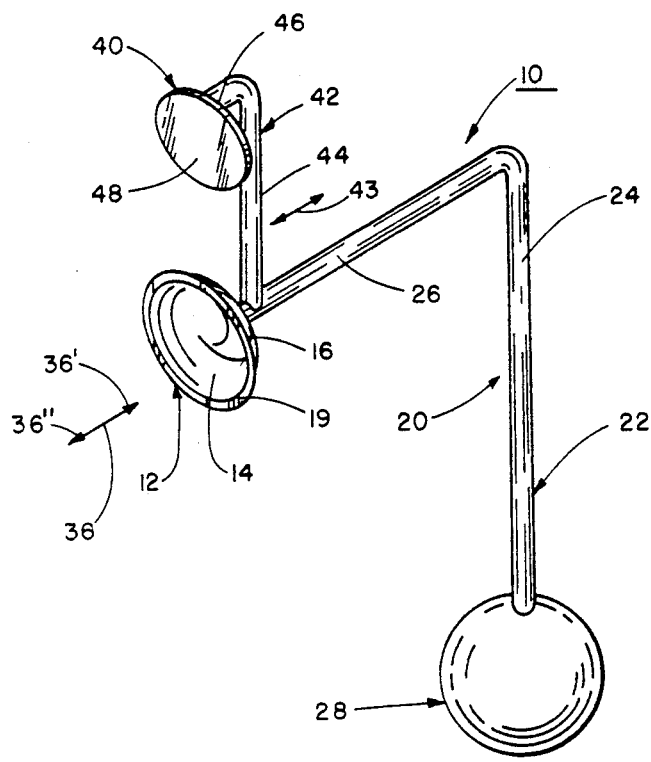
FIG. 1 is a perspective view showing the first embodiment of the contact lens holding and guiding accessory embodying the present invention.
Figure 2:
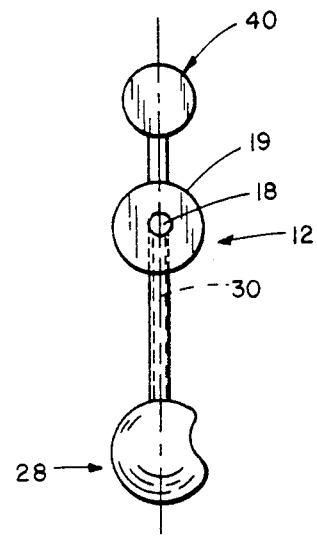
FIG. 2 is a front elevational view of the accessory.

Shown in FIGS. 1 and 2 is an accessory 10 for holding a contact lens as a user inserts the lens into his eye or removes the lens from his eye. The accessory also includes a means for guiding the user in such process, and can be used to immerse the lens in soaking or cleaning solution without requiring the user to touch the lens with his or her hands.

The accessory 10 includes a cup element 12 that is shaped and sized to hold a contact lens on a concave surface 14 thereof. The cup element includes a rear surface 16 which is convex, and the cup has an air passage 18 defined therethrough. The cup element is made of material that can be cleaned in water or in contact lens cleaning and soaking solution so that germs are not likely to be passed to the lens from the cup element. The cup element is used to hold and control the contact lens in place of the user's fingers, and can be cleaned easier and faster than the user's fingers or hands. The cup can also be used to move a contact lens in the user's eye to re-locate such lens, or the like. The cup element includes a rim 19 which is in a plane.

The cup element 12 is supported in position to move against a user's cornea or against a contact lens by a fluid circuit and support means 20. The means 20 includes an L-shaped bracket 22 having a long leg 24 and a short leg 26. The short leg 26 has one end thereof attached to the cup element, and the long leg has one end thereof mounted on a flexible ball 28. The bracket 22 is hollow and includes an air passage 30 therethrough, with the ball being hollow. The bracket is fluidically connected to the inside of the ball and to the air passage 18 so that air is moved from the ball out of the fluid passage as the ball is collapsed from the undistorted configuration shown in FIG. 1 towards the collapsed and distorted configuration shown in FIG. 2. Air then moves through the air passage 18 as the ball moves back to the undistorted FIG. 1 configuration from the FIG. 2 configuration. Air movement is indicated in FIG. 1 by the double-headed arrow 36. Movement in direction 36' causes a suction to be placed on a lens positioned near or against the concave surface 14, and movement of air in direction 36" forces a lens positioned adjacent to or on the concave surface 14 away from that surface. The ball is formed of elastomeric material or the like which has a memory so that it tends to restore itself to the undistorted FIG. 1 condition after it has been distorted into the FIG. 2 condition and released.

In this manner, a user can distort the ball 28, place the concave surface 14 near or against a contact lens, and then release the ball. The ball attempts to resort to the FIG. 1 undistorted position and move air through the air passage 18 in the direction 36'. However, the lens is impervious to such air movement, and is thus sucked towards and/or against the surface 14 and held there.

If the lens is in the user's eye, the held lens can be removed by simply moving the accessory away from the user's eye; or if the lens is not in the user's eye, the lens can be moved to any suitable location by moving the accessory 10. The lens can be immersed in storing or cleaning solution by simply immersing the cup element 12 into the solution, and flexing the ball 28 to further distort that ball. Such further distortion causes further air to move from the ball out of the air passage and against the lens located in the concave cup element. This further air movement is in the direction 36" and forces the lens away from the concave surface 14 thus releasing the lens from the accessory. The accessory is moved away from the lens before the ball is released so that solution is not sucked back into the conduit 30 or the lens is not captured again as the air moves in direction 36' as the ball restores itself to the undistorted FIG. 1 condition.

The accessory 10 further includes a guiding means for assisting the user in placing the concave surface 14 over or adjacent to a contact lens that is in place on the user's eye. This guiding means will be especially helpful to inexperienced contact lens wearers.

The guiding means shown in FIGS. 1 and 2 includes a magnifying mirror 40 that is mounted on the air conduit short leg 26 by an L-shaped bracket 42 having a long leg 44 fixed to the conduit short leg 26 and a short leg 46 supporting a planar mirror 48. The mirror 48 is positioned relative to the concave surface 14 so that the mirror abuts a user's forehead when the concave surface is in position over a contact lens in the user's eye. The mirror is planar and is thus located in a plane that is slightly in front of the plane containing concave cup element rim 19 to be located between the user's cornea and the cup element 14 when the mirror abuts the user's forehead. The slight suction created by releasing the distorted ball will be sufficient to move a lens off of a user's cornea and across a small gap between the concave surface 14 and the lens. Thus, the concave surface 14 need not be placed in contact with the lens to remove it from the user's eye.

The bracket 42 is shown in FIG. 1 as being fixedly mounted on the conduit short leg, but can also be movably mounted thereon by a clamp having a screw fastener such as will be later described. Movement of the bracket is indicated in FIG. 1 by the double-headed arrow 43. The mirror is used to guide the cup into position, and abutment between the mirror and the user's forehead is used to signal that the concave surface is close enough to the contact lens so that when the distorted ball 28 is released, it will suck the lens from the user's eye and against the concave surface 14.

Conversely, abutment between the mirror 48 and the user's forehead will signal that a lens held on the concave surface 14 is close enough to the user's eye so that a slight squeeze on the ball 28 will release the lens from the surface, and force the lens off of the concave surface and such released lens will move into position on the user's cornea. It is noted that the attraction of the lens to the cornea that occurs due to fluid attraction characteristics will move the lens from the concave surface onto the user's cornea without actually requiring that lens to contact the cornea prior to being forced away from the concave surface by air flowing in direction 36". Thus, the lens held on concave surface 14 need not be placed in contact with the user's cornea to move the lens from the concave surface onto the user's eye.

Figure 3:
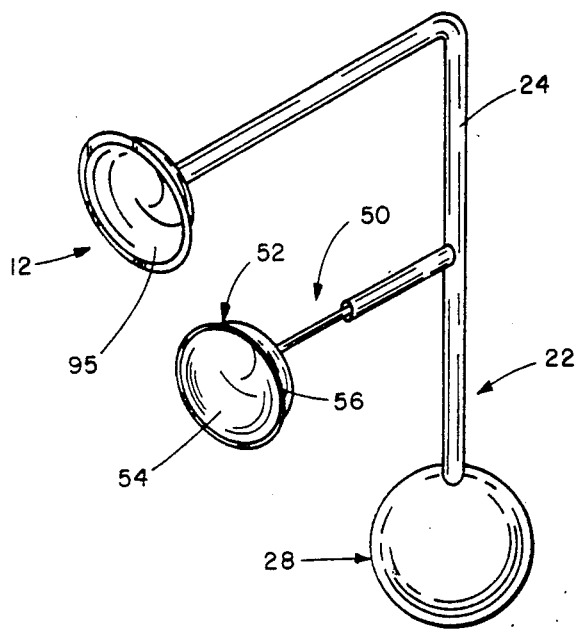
FIG. 3 is a perspective view showing a second embodiment of the contact lens holding and guiding accessory.

A further embodiment of the accessory is shown in FIG. 3 and includes a telescoping and expandable support arm 50. The support arm 50 has one end thereof attached to the conduit long leg 24 and supports a cheek-engaging cup element 52 on a distal end thereof. The cheek-engaging cup element 52 includes a concave surface 54 and a convex surface 56, and is sized and adapted to abut a user's cheek adjacent to that user's eye. This support arm thus serves to steady and guide the placement of the cup surface 14 against the contact lens or a lens supported on the concave surface 14 on the user's eye. The cup element 52 is shown to be similar in shape to the cup element 12, but can be elongated if suitable to produce a more stable mounting on the user's cheek.

Figure 6:
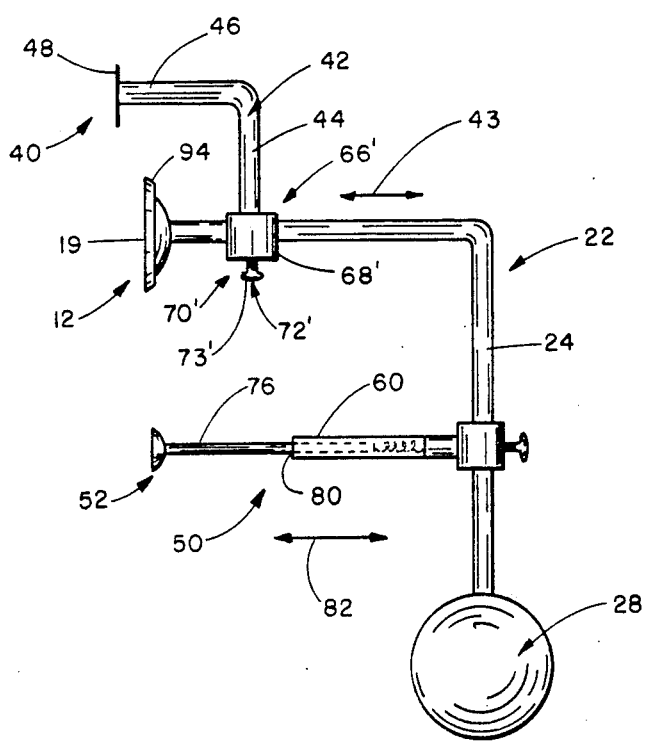
FIG. 6 is a side elevational view of the accessory.
Figure 4:
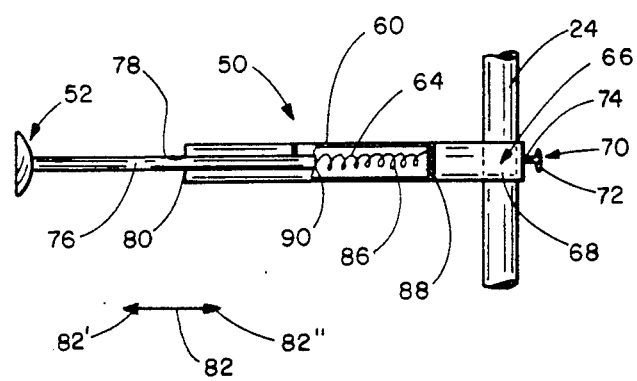
FIG. 4 is a side elevational view of a support arm used in the accessory of the present invention.

The support arm 50 is best shown in FIG. 4 as including a first tubular element 60 having the proximal end 62 thereof mounted to the leg 24 and being hollow to have a central bore 64 defined therethrough. The element 60 can be fixed to the leg 24 as shown in FIG. 3 or it can be movably mounted thereto by a clamp means 66 as shown in FIG. 4. The clamp means 66 includes a collar 68 that slidably surrounds the leg 24 and includes a hole defined therethrough. The collar includes screw threads mounted thereon adjacent to the hole, and a fastener 70 has a head 72 having a wing 73 and a body 74 that is threaded to co-operatively engage the threads on the collar so that the fastener can be threaded into the collar and into engagement with the short leg 24 to fix the support arm to that leg via the collar. As illustrated in FIG. 6, bracket 42 can be similarly slidably mounted to the conduit short leg 26 by a similar collar arrangement 60', with elements of collar 60' being identical to corresponding elements shown in FIG. 4 for collar 60, and thus having a prime notation.

The support arm further includes a second tubular element 76 that slidably fits into the first tubular element via a hole 78 defined in distal end 80 of that first tubular element. The sliding movement of the second element 76 with respect to the first element 60 is indicated in FIG. 4 by the double-headed arrow 82. Movement of the second element in direction 82' moves the cup element 52 closer to the user's face and movement of the second element in direction 82" moves the cup 52 away from the user's face.

The support arm also includes a spring element 86 located inside the first tubular element and having one end abutting a spring stop element 88 fixed to the first tubular element and having another end abutting a rear end 90 of the second element 76. The spring 86 is arranged to bias the second element 76 in the direction 82', and is compressed as the cup element 52 is pressed against the user's face. The spring can be compressed with gentle pressure and controls movement of the cup towards the user's eye so that no untoward movements will be executed which might damage the user's eye.

Figure 5:
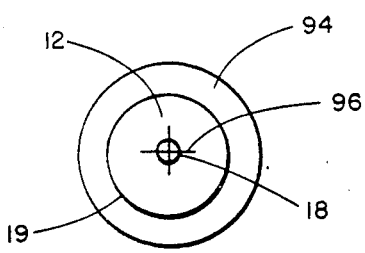
FIG. 5 is a front elevational view of a mirrored guiding element used in the accessory of the present invention.

A further embodiment of the accessory includes a mirror 94 that is located to circumnavigate the cup element 12. Such embodiment is shown in FIG. 5. The mirror 94 completely surrounds the cup element 12 and contacts the concave element rim 19 and permits the user to see the lens as it moves toward his eye or to see the cup element as it moves toward the lens on his eye. This mirror 94 will help the user properly place the cup with relation to his eye. The concave surface of the concave element 14 can also have a concave mirror 95 mounted thereon to further assist the user in guiding the concave element into position adjacent to his eye. The mirror 95 can also include a target 96 shown in FIG. 5 so the user can align his or her eye with the concave element for proper use thereof.

The accessory is formed of materials that are amenable to use with contact lenses and the cleaning and soaking solutions associated therewith, and which are amenable to being thoroughly cleaned.

It is understood that while certain forms of the present invention have been illustrated and described herein, it is not to be limited to the specific forms or arrangements of parts described and shown.

I claim:

1. An accessory for holding a contact lens comprising:
   A) a concave cup element having an air passage defined therethrough, said cup element having a concave surface which is sized and shaped to match the size and shape of a human cornea, and a convex surface and being adapted to engage and hold a contact lens, said cup element including an outer rim;
   B) fluid circuit and support means for moving air through said cup air passage, said fluid circuit and support means including
      (1) a flexible hollow ball made of material having a material memory so that when the ball is deformed, it will tend to return to an undeformed shape,
      (2) an L-shaped air conduit having a short leg connected at one end thereof to said concave cup element, a long leg, with another end of said short leg being connected to one end of said long leg and another end of said long leg being connected to said ball, said air conduit having an air passage defined therethrough and fluidically connecting said cup element air passage to the interior of said ball and conducting air through said air passage out of said air conduit as said ball is collapsed and through said air passage into said conduit as said collapsed ball regains an undistorted configuration; and
   C) a guiding means mounted on said air conduit adjacent to said cup element for assisting a user in guiding said cup element into position closely adjacent to that user's cornea, said guiding means including
      (1) an L-shaped bracket arm mounted on said air conduit adjacent to said concave cup element, said L-shaped bracket arm including a long leg attached to said air conduit and a short leg extending towards said concave cup element,
      (2) a planar magnifying mirror element mounted on said L-shaped bracket arm short leg to be spaced in front of a plane containing the rim of said concave cup element to be located between said cup element rim and the user's cornea,
      (3) an expandable support arm having a proximal end and a distal end and having said proximal end mounted on said air conduit and having a face-engaging element on said distal end, said support arm including
         (a) a first tubular element which is hollow to include a bore extending along a longitudinal axis thereof, said first tubular element being mounted on said air conduit and having a distal end spaced from said air conduit,
         (b) a hole defined through said first tubular element distal end,
         (c) a second tubular element slidably received through said first tubular conduit distal end hole and moving into and out of said first tubular element, said second tubular element having a rear end located inside of said first tubular element and a front end,
         (d) a spring stop mounted in said first tubular element and spaced from both said first tubular element distal end and from said first tubular element proximal end,
         (e) a spring element having one end thereof abutting said spring stop and another end thereof abutting said second tubular element rear end, said spring element biasing said second tubular element out of said first tubular element,
      (4) a first clamp element attaching said support arm to said air conduit, and including
         (a) a first collar surrounding said air conduit long leg and having a hole defined therethrough,
         (b) first screw threads on said collar adjacent to said first collar hole,
         (c) a first screw fastener threadably engaged with said first screw threads and having a wing head thereon,
      (5) connecting means connecting said L-shaped bracket arm long leg to said L-shaped air conduit short leg, said connecting means including a second clamp element having a second collar surrounding said L-shaped bracket arm short leg and having a hole defined therethrough, second screw threads on said second collar adjacent to said second collar hole, a second screw fastener threadably engaged with said second screw threads and having a wing head thereon,
      (6) a concave mirror on said concave cup element, said concave mirror having a target thereon,
      (7) an annular mirror on said cup element, said annular mirror circumnavigating said cup element and having an inner rim contacting said cup element outer rim with said cup element being located inside said annular mirror, and
      (8) said face-engaging element is mounted on said expandable support arm second tubular element front end.

* * * * *